United States Patent
Yakhno et al.

(10) Patent No.: US 7,350,403 B2
(45) Date of Patent: *Apr. 1, 2008

(54) METHOD AND APPARATUS FOR DETERMINATION OF FOOD QUALITY AND AUTHENTICITY

(75) Inventors: Tatjana Anatoljevna Yakhno, Nizhny Novgorod (RU); Anatoly Gennadievich Sanin, Nizhny Novgorod (RU); Vladimir Grigorievich Yakhno, Nizhny Novgorod (RU); Artem S. Pelushenko, Nizhny Novgorod (RU); Olga S. Shapovnikova, Nizhny Novgorod (RU); Michael B. Dowell, Hudson, OH (US); Christina V. Vacca, Avon, OH (US); Valentina B. Goutorova, Twinsburg, OH (US)

(73) Assignee: Aria Analyties, Inc., Cleveland, OH (US)

( * ) Notice: Subject to any disclaimer, the term of this patent is extended or adjusted under 35 U.S.C. 154(b) by 262 days.

This patent is subject to a terminal disclaimer.

(21) Appl. No.: 11/098,220

(22) Filed: Apr. 4, 2005

(65) Prior Publication Data

US 2005/0241373 A1 Nov. 3, 2005

Related U.S. Application Data

(63) Continuation-in-part of application No. 10/466,845, filed on Jul. 21, 2003, now Pat. No. 6,874,357.

(51) Int. Cl.
*G01N 29/00* (2006.01)
(52) U.S. Cl. .................. 73/64.53; 73/53.04; 73/61.73; 73/574

(58) Field of Classification Search .............. 73/64.53, 73/53.04, 61.73, 54.07, 61.74, 54.24, 24.01, 73/335.03, 335.06, 574, 342 R, 290 V, 290 R, 73/61.45, 61.77, 61.79
See application file for complete search history.

(56) References Cited

U.S. PATENT DOCUMENTS

| 2,876,083 | A | * | 3/1959 | Prietl ...................... 23/295 R |
| 5,706,815 | A | * | 1/1998 | Sarvazyan et al. .......... 600/438 |
| 5,798,452 | A | * | 8/1998 | Martin et al. ............... 73/32 R |
| 6,141,625 | A | * | 10/2000 | Smith et al. .................. 702/50 |
| 6,393,895 | B1 | * | 5/2002 | Matsiev et al. ............ 73/24.06 |

(Continued)

OTHER PUBLICATIONS

Angel Rodrieuez-Vazquez et al. A Method for Liquid Analysis by Means of Recording the Dynamics of Phase Tranistions During Drop Drying May 19-21, 2003.

(Continued)

*Primary Examiner*—Hezron Williams
*Assistant Examiner*—Jacques M. Saint-Surin

(57) ABSTRACT

A method for analysis of a multi-component fluid is provided based on the features of the dynamics of the self-organization processes in drying drops. An electro-acoustic resonator is utilized, with a drop of multi-component fluid placed on one end of the resonator. A shear oscillation is imparting to the resonator along its longitudinal axis. And oscillating electric voltage is placed across the resonator generally perpendicular to the direction of mechanical oscillation. Changes in the electrical conductance corresponding to changes in the acoustical-mechanical impedance can thereby be measured as the drop of multi-component liquid dries. The particular geometry of an amplitude curve includes identifying the spatio-temporal development and phase transitions is used for integral estimation of food authenticity and quality.

13 Claims, 3 Drawing Sheets

U.S. PATENT DOCUMENTS

| | | | | |
|---|---|---|---|---|
| 6,401,519 | B1* | 6/2002 | McFarland et al. | 73/24.06 |
| 6,494,079 | B1* | 12/2002 | Matsiev et al. | 73/24.05 |
| 6,725,707 | B1* | 4/2004 | Lin et al. | 73/54.01 |
| 6,854,338 | B2* | 2/2005 | Khuri-Yakub et al. | 73/861.27 |
| 6,874,357 | B2* | 4/2005 | Yakhno et al. | 73/64.53 |
| 6,904,786 | B2* | 6/2005 | Matsiev et al. | 73/24.06 |
| 6,957,565 | B2* | 10/2005 | Matsiev et al. | 73/24.06 |
| 7,043,969 | B2* | 5/2006 | Matsiev et al. | 73/54.41 |
| 7,073,370 | B2* | 7/2006 | Matsiev et al. | 73/24.06 |
| 2007/0241756 | A1* | 10/2007 | Mizukami et al. | 324/444 |

OTHER PUBLICATIONS

T. A. Yakhno et al. Study of the Dynamics of Phase Transitions in Liquids of Different Types by Measuring the Acoustomechanical Impedance of the Drying Drop Jul. 17, 2002.

T. A. Yakhno, et al. New Universal Electronic Tongue & Nose and its Possibilities in Food Examinations Sep. 24-26, 2003.

T. A. Yakhno et al. On the Existence of Regular Structures in Liquid Human Blood Serum (Plasma) and Phase Transitions in the Course of its Drying Sep. 3, 2002.

T. A. Yakhno et al. The Informative—Capacity Phenomenon of Drying Drops, Aptitude Test in Medical Diagnostics 2004.

T. A. Yakhno et al. Drying Drops of Biological Liquids: Dynamics of the Optical and Mechanical Properties. Application in Rapid Medical Diagnostics Dec. 22, 2004.

T. Yakhno et al. Dynamics of Phase Transitions in Drying Drops as an Information Parameter of Liquid Structure Jul. 2004.

* cited by examiner

METHOD AND APPARATUS FOR DETERMINATION OF FOOD QUALITY AND AUTHENTICITY

RELATED APPLICATIONS

The present invention is a continuation in part of Ser. No. 10/466,845 filed on Jul. 21, 2003, now U.S. Pat. No. 6,874,357, and incorporated by reference herein as if fully rewritten.

BACKGROUND OF THE INVENTION

1. Field of the Invention

The present invention relates generally to methods of assessing food authenticity and quality and, more particularly, to an apparatus for carrying out such methods utilizing the acousticomechanical impedance (AMI) characteristics associated with the properties of drying droplets of multi component liquids.

2. Description of the Related Art

The problem of rapid evaluation of food authenticity and quality is very topical today. Recent achievements in the infrared and mass spectroscopy, gas and liquid chromatography, nuclear magnetic resonance and microsensor engineering have been used to solve this problem; While experimental data are processed by the methods of modern mathematical analysis, obtaining necessary information usually requires the use of costly equipment and the involvement of highly qualified personnel. Moreover, estimation of the usefulness of a product is often based on determination of one or several components and cannot serve as a complete characteristic of its authenticity and quality.

Consequently, a need has been felt for providing an apparatus and method based on two phenomena: nonlinear dynamic processes in drying drops; and, a possibility of recoding these processes by means of a device developed for this task.

SUMMARY OF THE INVENTION

A sessile drop is a specific physical object. The initial shape of a drop is a function of its physical properties and substrate nature. In the same environment the following factors play a significant role in the dynamics of the drop drying process: surface tension, wettability, viscosity, inner structure, dispersion of colloids, heat conductance, ionic force, gel-forming substances, and cover skin density. Even the slightest variation in the composition of a liquid leads to the total change in these parameters during drop drying. These features make it possible to obtain "phase portraits"—the ID characteristic of liquids, which can be kept in a database and used as etalons for detecting counterfeits.

It is therefore an object of the present invention to provide technology to permit one to obtain the 10 characteristic of a product based on an inexpensive, compact device and combines high information capacity, universality and simplicity for use. Information retrieved from the dynamics of the mechanical characteristics of drops of studied liquids during their drying permits one to perform medical diagnostics, record the presence of smells and magnetic fields and determine the UV irradiation dose A feature of the present invention that is a radical difference from known prior art is that what is used as the informative parameter is the temporal dependence of the AMI of the drying drop as a unit.

Briefly described according to a preferred embodiment of the present invention, a drop of tested liquid of volume 5 microliters is dried on the surface of a quartz resonator oscillating with constant ultrasound frequency (60 kHz). This frequency is selected to agree with the resonance frequency of the unstrained resonator. The shear characteristics of the drop, which are extremely sensitive to the occurrence and increase in the new-phase structures on the surface between the drop and the quartz plate, are observed. The measured quantity is the dynamical complex conductance of the resonator, which is converted to the acoustical-mechanical impedance (AMI) of the drying drop, and the drying dynamics is displayed in the form of a curve.

In accordance with a preferred embodiment, temporal changes in the acoustical-mechanical impedance of a drying drop is expressed as the changers of its viscous and elastic properties.

An advantage of the present invention is that it allows for the integral identification of multicomponent liquids.

Another advantage of the present invention is that it allows for the identification of multi-component liquids based on the features of the dynamics of the self-organization processes in drying drops.

Yet another advantage of the present invention is it utilizes a software and hardware complex enabling one to record the dynamics of the acoustical-mechanical impedance of the drying drops that reflects the variation in their viscoelastic properties.

Further, algorithms for processing of experimental data are provided permitting one to automatically separate multicomponent liquids into groups depending on the task. By further developing this technology, it is possible to create a self-training device (or family of devices) for industrial and home use.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted in conjunction with the Figures.

1. Detailed Description of the Figures

Figure 1:
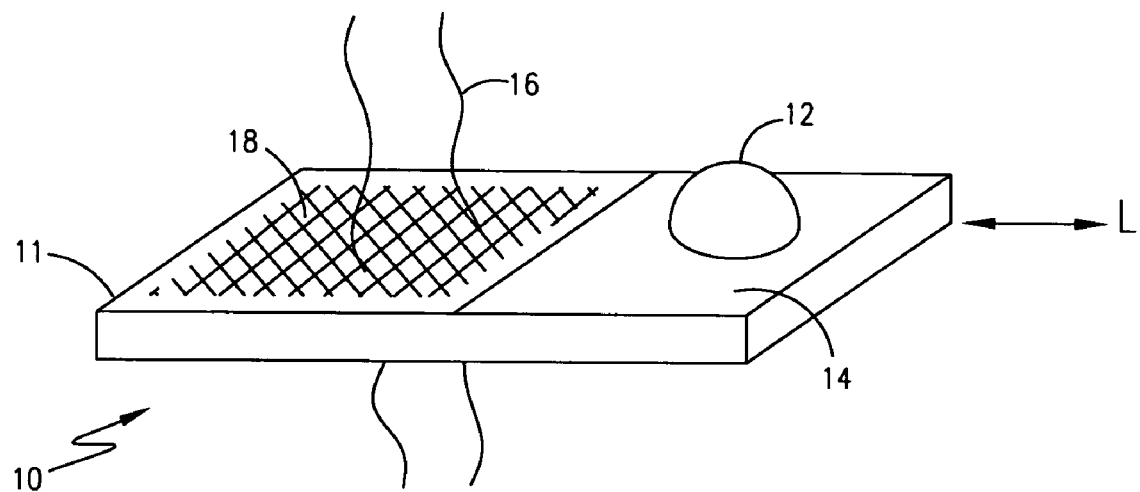
FIG. 1 is a pictorial design of the oscillation mode of a quartz resonator for use with the preferred embodiment of the present invention.
Figure 2:
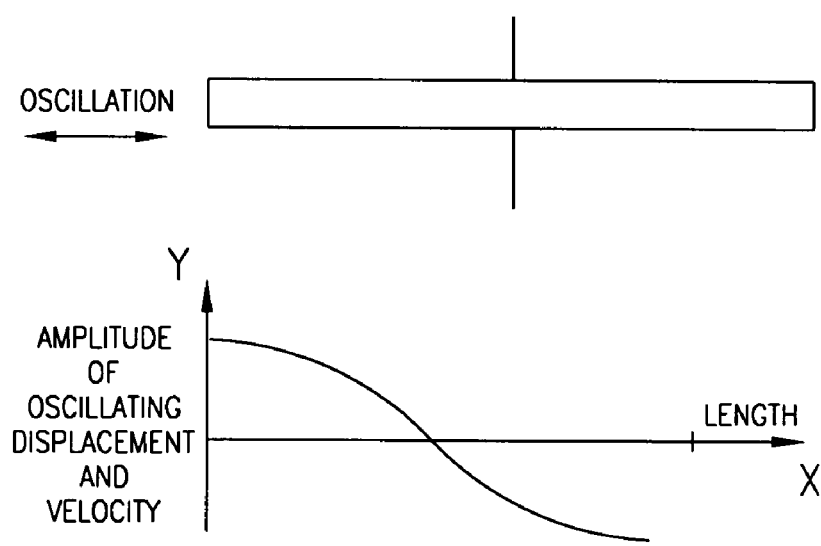
FIG. 2 is a diagramatic representation of the oscillatory velocity amplitude and longitudinal displacement of the resonator of FIG. 1.
Figure 3:
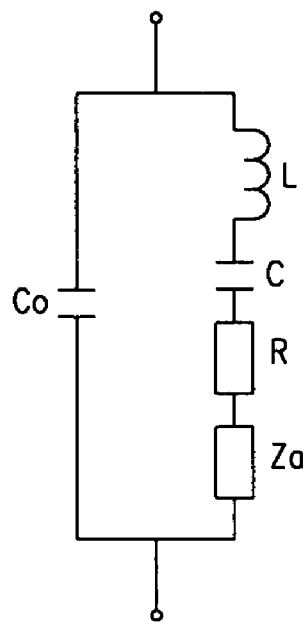
FIG. 3 is an electrical schematic of a resonator with one-side load according to a simplified equivalent of the present invention.

Measurement of the acoustical-mechanical impedance (hereinafter "AMI") is based on dependence of the electrical characteristics of the resonator on the physical properties of the liquid. This dependence is widely used in the studies of the properties of gases and liquids by means of electroacoustic resonators. As used to better understand the present disclosure, the measured electrical characteristics of a resonator are its resonance frequency and Q factor, which are changed when the resonator contacts the object under study. This property is used as the basis for determining such physical properties of a liquid as viscosity, density, concentration of sought substance, and so on. As shown in FIG. 1, the sensitive element is a resonator 10 in the form of a rectangular plate 11 (herein selected as that of quartz XYS/l °30' with section 48.0 by 4.5 by 1.0 mm). AMI variations of a drop 12 are recorded under conditions of shear oscillations of the resonator surface 14. Electrodes 16, on which an alternating voltage (selected herein as a sinusoidal voltage) is fed to excite mechanical oscillations, are applied on plane faces 18 having the largest area. The resonator 10 is fixed on the electrodes as wire conductors 16 soldered to the plate middle. The operating mode is the mode of longitudinal oscillations of the plate, i.e., compression-decompression oscillations in the direction perpendicular to the electric field applied. Shear displacements of all side faces of the plate occur in this case. Since the length of the plate is much larger than its width and height, the operating mode can be considered single-mode. The operating frequency of the excitation voltage corresponds to the frequency of the first longitudinal resonance of the plate, i.e., the plate length corresponds to one half of the length of the longitudinal sound wave in the resonator. In this case, the distribution of the oscillatory velocity amplitude over the plate length has a sinusoidal form with a zero value in the middle of the plate. A drop of a liquid 12 under study is placed on the end of the plate 11, i.e., where the oscillatory velocity amplitude of the surface is approximately constant. This end of the plate is for the operation. Part of the area of the electrodes 16 on the operating end of the plate 11 is removed to place the drop 12 directly on the surface of a quartz crystal. Under such conditions, the drop is an acoustic (mechanical) load of the resonator 10 for shear oscillations. The AMI of a drop 12 is determined from the electric conductance of the resonator 10 operated at a fixed frequency. As the theoretical model of the present embodiment, the scheme oscillatory velocity almost coincides with the oscillatory velocity of the butt. At frequncies close to the resonant frequency, the equivalent scheme of a resonator with a one-side load can be reduced to the form shown in FIG. 3. All the elements of this scheme have electrical dimensions, and their nominal values depend on the sizes of the resonator 10 and the characteristics of the piezo material. The capacitance Co corresponds to the static capacitance of the resonator. The elements L, C, R, and Za form the so-called dynamic branch of the scheme. The resistor R corresponds to taking into account the intrinsic losses of the resonator. The introduced impedance Za is directly proportional to the acoustic impedance of the resonator load (the complex impedance Zd of a drop in this case):

$$Za = K1 * Zd \qquad (1)$$

The value of the effective proportionality coefficient K1 is determined by the parameters of the piezo plate. It should be noted that the overall impedance of the resonator plus load, Za, incorporates within it the integral impedance of the overall device, in addition to the impedance added by the measured load and is utilized as an overall instrument constant. It is anticipated that in the future the ability may exist to measure separately the instrument impedance, unloaded, and a specific load impedance representative of the sample itself. Such an improvement could theoretically allow for quantification of results that may have specific, useful meaning, such as for those applications in which the test sample itself is physically representative of the actual end use of the product being tested, i.e. films, coatings, etc.

The complex electric conductance Y of the resonator is written in the form $$Y = \frac{1}{Za + R + j^*\omega^*L - j/\omega^*C} + j^*\omega^*C_0, \qquad (2)$$

where ω is the circular frequency and j is imaginary unity.

Figure 4:
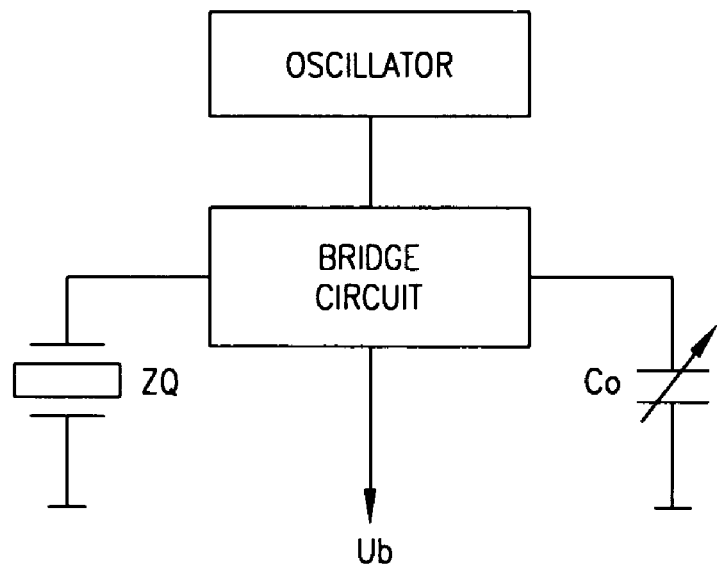
FIG. 4 is a simplified electrical schematic of the switch-on of the resonator (ZQ) in a bridge circuit for use therein.

Expression (2) describes the relation between the electric conductance of the resonator and the quantity Zd of the drop AMI (entering Za). The introduced impedance Za, as Zd, is complex. For the measurements, we used the bridge circuit in which the imbalance voltage is proportional to the difference of currents in the bridge arms. *A resonator is included in one branch of the bridge circuit, and a capacitor with capacitance equal to the static magnitude $C_0$ of a quartz resonator (FIG. 4**), in another branch. An alternating voltage, anticipated in its preferred embodiment as a sinusoidal voltage, from the oscillator is fed to the bridge circuit.

$$Y = \frac{1}{Za + R} + j^*\omega^*C_0. \qquad (3)$$

Under these conditions, the complex amplitude of the imbalance voltage Ub of the bridge circuit (which is proportional to the difference of currents in the bridge arms) can be written as:

$$Ub = K2^*(Y - j^*\omega^*C_0) = K2^*\frac{1}{Za + R} = K2^*\frac{1}{K1^*Zd + R'} \qquad (4)$$

where K2 is the constant of the measuring instrument.

Figure 5:
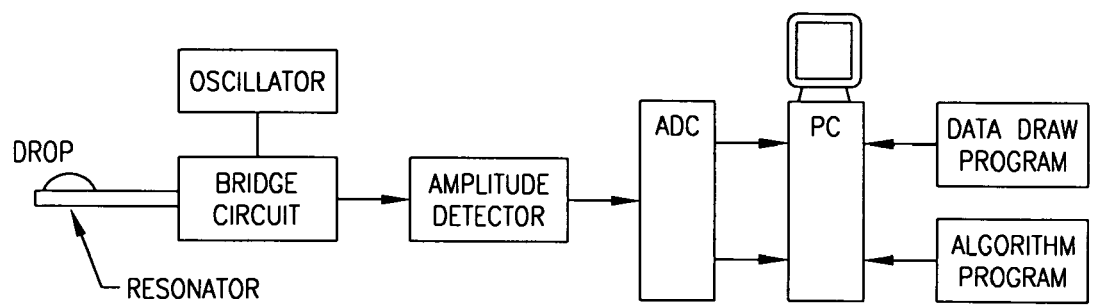
FIG. 5 is a block diagram of a method for utilization of the present invention.

The resistor magnitude R can easily be determined experimentally by means of an additional measurement using a resonator without the drop, i.e., for Za=0. The resistor magnitude R (intrinsic losses in the resonator) is of the order of 2000 Ohm, which is considerably smaller than the modulus of the impedance IZaI, which varies during drying from several tens of thousands to several hundreds of thousands of Ohms. Equation (4) illustrates the principle of experimental determination of the complex impedance Zd of a drop. Measuring the complex value of the imbalance voltage Ub of the bridge circuit and knowing the constants K1 and K2, one can calculate the desired value of Zd. The variant of the device used to obtain the results presented here is shown in FIG. 5. An amplitude detector 50 detects the output voltage of the bridge circuit 52. This signal is fed through an analogue-to-digital converter (ADC) 54 to a personal computer (PC) 56. The drop drying process is displayed in the form of an amplitude curve corresponding to the modulus of the AMI. The mode of mapping and accumulation of data is ensured by the data-draw program. Upon completion of recording, data are processed using a certain algorithm of the algorithm program.

2. Operation of the Preferred Embodiment

By way of example, and not as a limitation, the operation of the present invention can be demonstrated by discussion of various sample analyses in which a drop of studied liquid of volume 5 μl, kept under room conditions (T=18-22° C., P=740-760 Hg mm, and H=60%-70%), is placed onto the operating part of the resonator 10 using a micropipette. To protect against external streams of air, the measuring element of the device can be covered by a cap. Software allows the dynamics of the measured quantities to be followed in real time on a display. When recording is complete, the result is saved to a database.

It has been shown that salt-containing liquids usually have one peak on the AMI curve, which corresponded salt crystallization process. Further, when a drop of colloid liquid begins to dry on a solid plate, it goes through some phase transitions. The main of them are gel matric formation and salt crystallization. Both these processes are extremely sensitive to liquid composition. These consequences of events were observed in drying drops of colloids: the first was the gel matrix formation and the second was the salt crystallization. It is clear, that the drying process is governed by water evaporation intensity. And this parameter depends on gel matrix quality and cover skin density over the drop. Thus, the AMI dynamics of drying drop contains the integral information about tested liquid and can be used for description the liquid as a whole.

Figure 6:
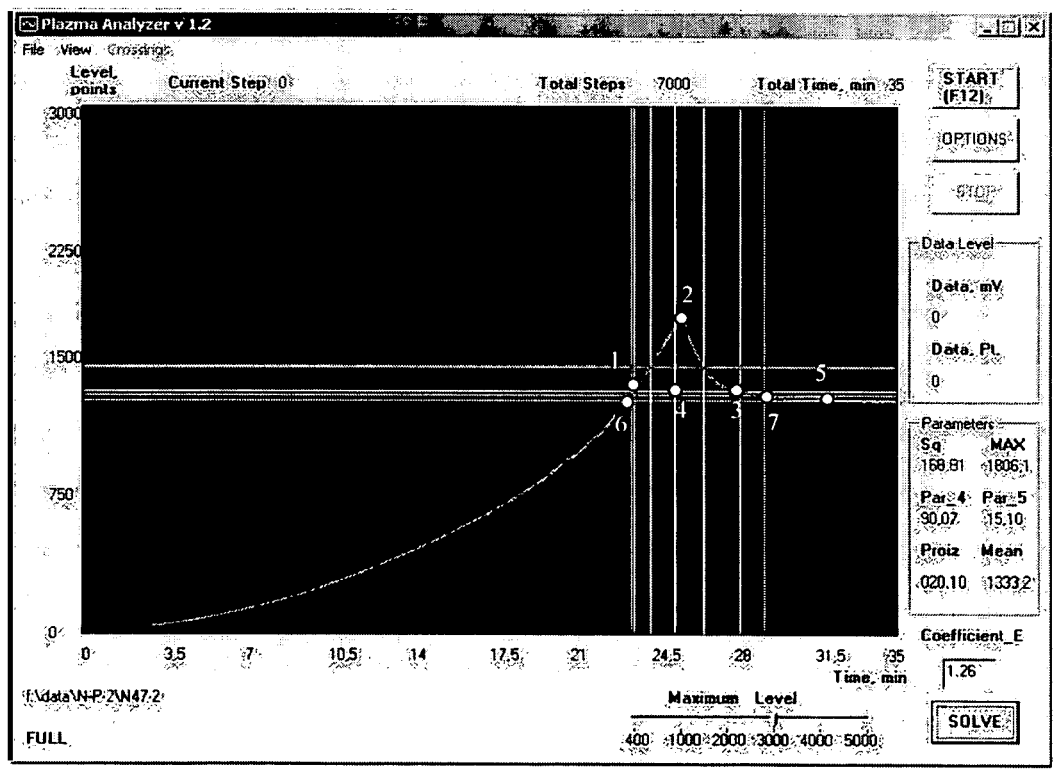
FIG. 6 is an interface of software in the mode of automatic search for given reference points on the AMI curve for calculation of shape indices using given algorithms.

As shown in FIG. 6, in analyzing mainly the particular geometry of this part of the AMI curves, reference points are chosen automatically on the curve to calculate the pre-assigned parameters characterizing the particular features of the curve shape. After the drop dries completely, calculation of the resulting curve is almost instantaneous. The compared results are presented in the form of an arithmetic mean with two standard deviations (M±σ) or on a plane in the coordinates of the parameters of different algorithms (shape indexes).

The foregoing descriptions of specific embodiments of the present invention have been presented for purposes of illustration and description. Thus, the technology we develop is a simple universal instrument enabling one to determine in one stage the quality of various liquid products in microdoses. Comparing it with known analytical methods by such parameters as simplicity of use and cost, this technology is close to organoleptic, but is different from the latter by the absence of limitations related to harmful components and objectiveness (obtaining easy-to formalize numerical results). This is not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents. Therefore, the scope of the invention is to be limited only by the following claims.

What is claimed is:

1. A method for analysis of a multi-component fluid based on the features of the dynamics of the self-organization processes in drying drops, said method comprising the steps:
   a. Selecting an electro-acoustic resonator having a first side opposite a second side along a longitudinal axis;
   b. Placing a drop of multi-component fluid on said first side;
   c. Imparting an oscillation on said resonator along said longitudinal axis at said second side; and
   d. Measuring the changes caused in the acoustical mechanical impedance caused to said resonator as said drop dries.

2. The method of claim 1, wherein said imparted oscillation is a shear oscillation imparted at a constant frequency.

3. The method of claim 2, wherein said imparted oscillation is of a sinusoidal form.

4. The method of claim 3, wherein said imparted oscillation corresponds to a frequency of the first longitudinal resonance of said resonator.

5. The method of claim 1, wherein said resonator comprises a rectangular plate of quartz.

6. The method of claim 1, wherein said measuring comprises:
   a. Applying an electric field to said resonator in a direction perpendicular to said imparted oscillation;
   b. Tracking the electric conductance of said resonator as said drop dries;
   c. Generating an amplitude curve from said tracking that corresponds to the modulus of the acoustic-mechanical impedance of said resonator-drop combination;
   d. Mapping said amplitude curve; and
   e. Analyzing the particular geometry of said amplitude curve.

7. The method of claim 6, wherein said analyzing of said particular geometry of said amplitude curve includes comparing said mapped amplitude curve against a known amplitude curve.

8. The method of claim 7, wherein said known amplitude curves allow one to automatically separate liquids into groups.

9. The method of claim 6, wherein said analyzing of said particular geometry of said amplitude curve includes identifying the spatio-temporal development and phase transitions when a solvent is evaporated.

10. The method of claim 9, wherein said spatio-temporal development and phase transitions is used for integral estimation of food authenticity and quality.

11. The method of claim 10, wherein said food is selected from the group comprising water, carbonated drinks, juices, milk, dairy products, and alcoholic beverages.

12. The method of claim 9, wherein the dynamics of said acoustal-mechanical impedance of the drying drops that reflects the variation in their viscoelastic properties is used as an identifying characteristic of a liquid.

13. The method of claim 1, wherein said resonator comprises:
   a rectangular plate of quartz capable of receiving a drop of multi-component liquid at one end;
   a plurality of electrical conductors affixed tot he center of said rectangular plate and in electrical communication with an excitation voltage;
   means for imparting longitudinal mechanical oscillation to said rectangular plate; and
   means for measuring the changes in the excitation voltage; wherein changes in the excitation voltage caused by the drying of said drop on said plate corresponds to said acoustal-mechanical impedance of said plate-drop combination.

* * * * *